(12) United States Patent
Li

(10) Patent No.: US 12,195,464 B2
(45) Date of Patent: Jan. 14, 2025

(54) LUMATEPERONE BIS-TOSYLATE SALTS AND CRYSTALS AND METHODS FOR MANUFACTURE THEREOF

(71) Applicant: INTRA-CELLULAR THERAPIES, INC., New York, NY (US)

(72) Inventor: Peng Li, New Milford, NJ (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 0 days.

(21) Appl. No.: 17/652,076

(22) Filed: Feb. 22, 2022

(65) Prior Publication Data
US 2022/0281867 A1  Sep. 8, 2022

Related U.S. Application Data

(63) Continuation of application No. 16/714,139, filed on Dec. 13, 2019, now abandoned, which is a continuation of application No. PCT/US2019/035845, filed on Jun. 6, 2019.

(60) Provisional application No. 62/681,534, filed on Jun. 6, 2018.

(51) Int. Cl.
*C07D 471/16* (2006.01)

(52) U.S. Cl.
CPC ........ *C07D 471/16* (2013.01); *C07B 2200/13* (2013.01)

(58) Field of Classification Search
CPC .......................... C07D 471/16; C07B 2200/13
See application file for complete search history.

(56) References Cited

U.S. PATENT DOCUMENTS

| | | | |
|---|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,115,577 A | 9/1978 | Rajagopalan |
| 4,183,936 A | 1/1980 | Rajagopalan |
| 4,219,550 A | 8/1980 | Rajagopalan |
| 4,238,607 A | 12/1980 | Rajagopalan |
| 4,522,944 A | 6/1985 | Doria et al. |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,576,460 A | 11/1996 | Buchwald et al. |
| 5,648,539 A | 7/1997 | Goodbrand et al. |
| 5,648,542 A | 7/1997 | Goodbrand et al. |
| 5,654,482 A | 8/1997 | Goodbrand et al. |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,847,166 A | 12/1998 | Buchwald et al. |
| 5,902,901 A | 5/1999 | Goodbrand et al. |
| 6,043,370 A | 3/2000 | Kubo et al. |
| 6,166,226 A | 12/2000 | Buchwald et al. |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,465,693 B2 | 10/2002 | Buchwald et al. |
| 6,541,639 B2 | 4/2003 | Zhou et al. |
| 6,548,493 B1 | 4/2003 | Robichaud et al. |
| 6,552,017 B1 | 4/2003 | Robichaud et al. |
| 6,699,852 B2 | 3/2004 | Robichaud et al. |
| 6,713,471 B1 | 3/2004 | Robichaud et al. |
| 6,759,554 B2 | 7/2004 | Buchwald et al. |
| 6,762,329 B2 | 7/2004 | Marcoux et al. |
| 6,849,619 B2 | 2/2005 | Robichaud et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |

(Continued)

FOREIGN PATENT DOCUMENTS

| | | |
|---|---|---|
| EP | 0 856 508 A1 | 8/1998 |
| EP | 1 245 553 A2 | 10/2002 |

(Continued)

OTHER PUBLICATIONS

Balbach, et al. "Pharmaceutical evaluation of early development candidates 'the 100 mg-approach', " International Journal of Pharmaceutics, vol. 275, pp. 1-12 (2004).

(Continued)

*Primary Examiner* — Susanna Moore

(74) *Attorney, Agent, or Firm* — Hoxie & Associates LLC

(57) ABSTRACT

The disclosure provides a new, stable, pharmaceutically acceptable bis-tosylate salt form of 1-(4-fluoro-phenyl)-4-((6bR,10aS)-3-methyl-2,3,6b,9,10,10a-hexahydro-1H,7H-pyrido[3',4': 4,5]pyrrolo[1,2,3-de]quinoxalin-8-yl)-butan-1-one:

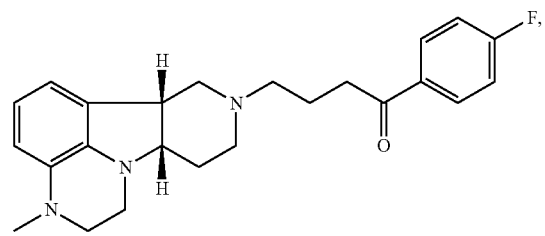

together with methods of making and using them, and pharmaceutical compositions comprising them.

9 Claims, 7 Drawing Sheets

(56) References Cited

U.S. PATENT DOCUMENTS

| | | |
|---|---|---|
| 7,071,186 B2 | 7/2006 | Robichaud et al. |
| 7,081,455 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,870 B2 | 5/2007 | Ghosh et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,462,641 B2 | 12/2008 | Igo et al. |
| 7,592,454 B2 | 9/2009 | Lee et al. |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,598,119 B2 | 12/2013 | Mates et al. |
| 8,648,077 B2 | 2/2014 | Tomesch et al. |
| 8,779,139 B2 | 7/2014 | Tomesch et al. |
| 8,993,572 B2 | 3/2015 | Mates et al. |
| 9,168,258 B2 | 10/2015 | Mates et al. |
| 9,199,995 B2 | 12/2015 | Tomesch et al. |
| 9,315,504 B2 | 4/2016 | Tomesch et al. |
| 9,371,324 B2 | 6/2016 | Mates et al. |
| 9,428,506 B2 | 8/2016 | Mates et al. |
| 9,586,960 B2 | 3/2017 | Tomesch et al. |
| 9,616,061 B2 | 4/2017 | Mates et al. |
| 9,708,322 B2 | 7/2017 | Peng et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,221,176 B2 | 3/2019 | Tomesch et al. |
| 10,322,134 B2 | 6/2019 | Mates et al. |
| 10,464,938 B2 | 11/2019 | Tomesch et al. |
| 10,472,359 B2 | 11/2019 | Li et al. |
| 10,597,395 B2 | 3/2020 | Tomesch et al. |
| 10,654,854 B2 | 5/2020 | Li et al. |
| 10,688,097 B2 | 6/2020 | Yao et al. |
| 10,702,522 B2 | 7/2020 | Vanover et al. |
| 10,844,061 B2 | 11/2020 | Li et al. |
| 10,960,009 B2 | 3/2021 | Vanover et al. |
| 10,960,010 B2 | 3/2021 | Vanover et al. |
| 11,014,925 B2 | 5/2021 | Li et al. |
| 11,026,951 B2 | 6/2021 | Vanover et al. |
| 11,053,245 B2 | 7/2021 | Mates et al. |
| 11,066,407 B2 | 7/2021 | Tomesch et al. |
| 11,124,514 B2 | 9/2021 | Mates et al. |
| RE48,825 E | 11/2021 | Tomesch et al. |
| 11,407,751 B2 | 8/2022 | Tomesch et al. |
| 11,440,911 B2 | 9/2022 | Wennogle et al. |
| 11,453,670 B2 | 9/2022 | Li et al. |
| 2001/0008942 A1 | 7/2001 | Buchwald et al. |
| 2004/0034015 A1 | 2/2004 | Robichaud et al. |
| 2004/0127482 A1 | 7/2004 | Robichaud et al. |
| 2004/0182749 A1 | 9/2004 | Domokos et al. |
| 2004/0186094 A1 | 9/2004 | Robichaud et al. |
| 2004/0220178 A1 | 11/2004 | Robichaud et al. |
| 2005/0222209 A1 | 10/2005 | Zeldis et al. |
| 2005/0239768 A1 | 10/2005 | Lee et al. |
| 2006/0128713 A1 | 6/2006 | Jolidon et al. |
| 2006/0148808 A1 | 7/2006 | Robichaud et al. |
| 2006/0205787 A1 | 9/2006 | Muller et al. |
| 2007/0066677 A1 | 3/2007 | Igo et al. |
| 2007/0203120 A1 | 8/2007 | McDevitt et al. |
| 2010/0204470 A1 | 8/2010 | Wieser et al. |
| 2011/0112105 A1 | 5/2011 | Tomesch et al. |
| 2014/0050783 A1 | 2/2014 | Mates et al. |
| 2014/0323491 A1 | 10/2014 | Tomesch et al. |
| 2014/0364609 A1 | 12/2014 | Mates et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2015/0166540 A1 | 6/2015 | Mates et al. |
| 2016/0031885 A1 | 2/2016 | Li et al. |
| 2016/0194326 A1 | 7/2016 | Tomesch et al. |
| 2016/0310502 A1 | 10/2016 | Vanover et al. |
| 2017/0319580 A1 | 11/2017 | Yao et al. |
| 2018/0271862 A1 | 9/2018 | Li et al. |
| 2019/0112309 A1 | 4/2019 | Li et al. |
| 2019/0112310 A1 | 4/2019 | Li et al. |
| 2019/0211015 A1 | 7/2019 | Mittelman et al. |
| 2019/0231780 A1 | 8/2019 | Yao et al. |
| 2020/0102309 A1 | 4/2020 | Li et al. |
| 2020/0148683 A1 | 5/2020 | Peddy et al. |
| 2021/0070755 A1 | 3/2021 | Berecz et al. |
| 2022/0363682 A1 | 11/2022 | Wennogle et al. |

FOREIGN PATENT DOCUMENTS

| | | | |
|---|---|---|---|
| EP | 1 254 884 A2 | 11/2002 | |
| EP | 1 564 671 A1 | 1/2005 | |
| WO | WO 1999/043643 A3 | 9/1999 | |
| WO | WO 2000/002887 A3 | 1/2000 | |
| WO | WO 2000/064899 A1 | 11/2000 | |
| WO | WO 2004/039788 A1 | 5/2004 | |
| WO | WO 2007/025103 A2 | 3/2007 | |
| WO | WO 2009/017836 A1 | 2/2009 | |
| WO | WO 2009/100324 A1 | 8/2009 | |
| WO | WO-2018031535 A1 * | 2/2018 | ........... C07C 309/30 |
| WO | WO 2018/106916 A1 | 6/2018 | |
| WO | WO 2019/102240 A1 | 5/2019 | |

OTHER PUBLICATIONS

Bastin, "Salt Selection and Optimized Procedures for Pharmaceutical New Chemical Entities", Organic Process and Research Development, vol. 4, No. 5, pp. 427-435 (2000).

Byrn, "Pharmaceutical Solids: A Strategic Approach to Regulatory Considerations," vol. 12, No. 7, pp. 945-954 (1995).

Davis, et al. "ITI-007 demonstrates brain occupancy at serotonin 5-HT2A and dopamine D2 receptors and serotonin transporters using positron emission tomography in healthy volunteers," Psychopharmacology, Published Online Apr. 7, 2015, 10 pages.

Davis, et al., "ITI-007 in the treatment of schizophrenia: from novel pharmacology to clinical outcomes," Expert Review of Neurotherapeutics, vol. 16, No. 6, pp. 601-614 (2016).

Gadade, et al., "Pharmaceutical Cocrystals: Regulatory and Strategic Aspects, Design and Development," Adv Pharm Bull, vol. 6, No. 4, pp. 479-494, (2016).

Grant, "Polymorphism in Pharmaceutical Solids", Chapter 1, pp. 1-10 (1999).

Guillory, "Polymorphism in Pharmaceutical Solids", Chapter 5, pp. 183-226 (1999).

Haynes, "Occurrence of Pharmaceutically Acceptable Anions and Cations in the Cambridge Database," Journal of Pharmaceutical Sciences, vol. 94, No. 10, pp. 2111-2120 (2005).

International Search Report for International Application No. PCT/US2009/003261, mailed Jul. 16, 2009, 3 pages.

International Search Report for International Application No. PCT/US2017/024562, mailed Jun. 27, 2017, 2 pages.

International Search Report for International Application No. PCT/US2017/024597, mailed Jun. 27, 2017, 3 pages.

International Search Report for International Application No. PCT/US2018/052922, mailed Nov. 26, 2018, 3 pages.

International Search Report and Written Opinion of International Application No. PCT/US2019/035845, prepared by the International Searching Authority, date mailed: Sep. 5, 2019, 7 pages.

Jain, et al., "Polymorphism in Pharmacy", Indian Drugs, vol. 23, No. 6, pp. 315-316 (1986).

Lee, et al., "Novel, Highly Potent, Selective 5-HT2A/D2 Receptor Antagonists as Potential Atypical Antipsychotics," Bioorg. Med. Chem. Lett., vol. 13, p. 767-770, (2003).

Li, et al., "Discovery of a Tetracyclic Quinoxaline Derivative as a Potent and Orally Active Multifunctional Drug Candidate for the Treatment of Neuropsychiatric and Neurological Disorders," vol. 57, pp. 2670-2682 (2014).

(56) References Cited

OTHER PUBLICATIONS

Li, et al., "Dopamine Targeting Drugs for the Treatment of Schizophrenia: Past, Present and Future," Current Topics in Medicinal Chemistry, vol. 16, pp. 3385-3403 (2016).
Marek, et al., "Synergistic Action of 5-HT2A Antagonists and Selective Serotonin Reuptake Inhibitors in Neuropsychiatric Disorders," Neuropsychopharmacology, vol. 28, pp. 402-412 (2003).
Murakami, et al., Chem. Pharm. Bull, vol. 43, No. 8, pp. 1281-1286, (1995).
Nagai, et al., "Synthesis of 2, 3, 4, 4a, 5, 9b-hexahydro-1H-pyrido [4,3-b] indole derivatives and their central nervous system activities." Journal of Medicinal Chemistry, vol. 22, No. 6, pp. 677-683, (1979).
Newman, et al., "Solid-State Analysis of the Active Pharmaceutical Ingredient in Drug Products," Drug Discovery Today, vol. 8, No. 9, pp. 898-903 (2003).
Perlis, et al., "Clinical Features of Bipolar Depression Versus Major Depressive Disorder in Large Multicenter Trials," Am J Psychiatry, vol. 163, pp. 225-231, (2006).
Rubí, et al., "Minireview: New Roles for Peripheral Dopamine on Metabolic Control and Tumor Growth: Let's Seek the Balance," Endocrinology, vol. 151, No. 12, pp. 5570-5581, (2010).
Savjani et al., "Drug Solubility: Importance and Enhancement Techniques," International Scholarly Research Network Pharmaceutics (2012), vol. 2012, pp. 1-10.
Singhal, et al., "Drug polymorphism and dosage form design: a practical perspective", Advanced Drug Delivery Reviews, vol. 56, pp. 335-347 (2004).
Snyder, et al., "Functional Profile of a Novel Modulator of Serotonin, Dopamine, and Glutamate Neurotransmission," Psychopharmacology, vol. 232, pp. 605-621 (2015).
Vippagunta, et al., "Crystalline Solids," Advanced Drug Delivery Reviews, vol. 48, 24 pages, (2001).
Written Opinion of International Application No. PCT/US2019/035845, issued by the International Searching Authority on Sep. 5, 2019, 4 pages.
Bavin, M, "Polymorphism in Process Development," Chemistry & Industry, pp. 527-529 (1989).
Berge, S. et al., "Pharmaceutical Salts," J. Pharm. Sci. 66(1):1-19 (1977).
Caira, MR, "Crystalline Polymorphism of Organic Compounds," Topics in Current Chemistry, vol. 198, p. 163-203 (1998).
Ich, "Specifications: Test Procedures and Acceptance Criteria for New Drug Substances and New Drug Products: Chemical Substances," ICH Harmonized Tripartite Guideline (Oct. 6, 1999).
Jozwiakowsi, MJ, Liu, R (Ed.), "Alteration of the Solid State of the Drug Substance: Polymorphs, Solvates, and Amorphous Forms," Water-Insoluble Drug Formulation, Interpharm Press, pp. 525, 557-561 (2000).
Serajuddin, ATM, "Salt formation to improve drug solubility," Advanced Drug Delivery Reviews, 59:603-616 (2007).
Stahl & Wermouth (Eds.), "Handbook of Pharmaceutical Salts Properties, Selection, and Use," Wiley-VCH, pp. 167-168, 170-173, 216-217 (2002).
Stahl & Wermouth (Eds.), "Handbook of Pharmaceutical Salts Properties, Selection, and Use," Wiley-VCH, pp. 258-261 (2002).
Barman et al., "Newer Antipsychotics: Brexpiprazole, Cariprazine, and Lumateperone: A Pledge or Another Unkept Promise?," World J. Psychiatr., vol. 11, No. 12, p. 1228-38 (2021).
Bharate, S.S., "Recent Developments in Pharmaceutical Salts: FDA Approvals From 2015 to 2019," Drug Discovery Today, vol. 26, No. 2, p. 384-398, (2021).
Brittain et al., "Chapter 5: Generation of Polymorphs, Hydrates, Solvates, and Amorphous Solids," Polymorphism in Pharmaceutical Solids, 25 pages, (1999).
Correll et al., "Efficacy and Safety of Lumateperone for Treatment of Schizophrenia a Randomized Clinical Trial," JAMA Psychiatry, vol. 77, No. 4, p. 349-358 (2020).
Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary P93).
Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).
Edinoff et al., "Lumateperone for the Treatment of Schizophrenia," Psychopharmacology Bulletin, vol. 50, No. 4, p. 32-59 (2020).
Gramigna, J, "Lumateperone Safe, Effective for Depressive Symptoms Among Patients with Bipolar Disorders," American Society of Clinical Psychopharmacology Annual Meeting, Jun. 2, 2020, 3 pages.
Guillory, J.K., "Generation of Polymorphs, Hydrates, Solvates, and Amorphous Solids", Polymorphism in Pharmaceutical Solids, Chapter 5, pp. 183-226, (1999).
Hlavinka, E., "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.
Khorana et al., "Gamma-Carbolines: Binding at 5-HT5A Serotonin Receptors," Bioorganic & Medicinal Chemistry, vol. 11, pp. 717-722, p. 718 Table 1, (2003).
Lieberman et al., "ITI-007 for the Treatment of Schizophrenia: A 4-Week Randomized, Double-Blind, Controlled Trial," Biol. Psychiatry, vol. 79, No. 12, pp. 952-961, (2015).
O'Gorman, et al., "Lumateperone (ITI-007): A Novel Investigational Agent with Broad Therapeutic Potential Across Multiple Neuropsychiatric Disorders," Poster P.1.g.038, European College of Neuropsychopharmacology (ECNP) Congress (2017).
Peterson et al., "Expanding the Scope of Crystal Form Evaluation in Pharmaceutical Science," J Pharm Pharmaceut Sci., vol. 9, No. 3, p. 317-326, (2006).
Press Release, "Intra-Cellular Therapies Reports Positive Final Results of a Phase II Clinical Trial With ITI-007 in Patients with Sleep Maintenance Insomnia.", Intra-Cellular Therapies, Press Release Date: Mar. 10, 2009, 3 pages, available at: https://ir.intracellulartherapies.com/static-files/375e1667-6457-4cd9-95dc-616ca3b5d02b.
Press Release, "Intra-Cellular Therapies Announces Top-Line Results from the Second Phase 3 Trial of ITI-007 in Patients with Schizophrenia (Study '302)", Intra-Cellular Therapies, Press Release Date: Sep. 28, 2016, 8 pages, available at: https://globenewswire.com/news-release/2016/09/U.S. Appl. No. 28/875,435/0/en/Intra-Cellular-Therapies-Announces-Top-Line-Results-from-the-Second-Phase-3-Trial-of-ITI-007-in-Patients-with-Schizophrenia-Study-302.html.
Press Release, "Intra-Cellular Therapies Announces Additional Results From Phase I/II Clinical Trial for ITI-007 in Healthy Geriatric Subjects and Patients With Dementia.", Intra-Cellular Therapies, Press Release Date: Nov. 21, 2014.
Saal et al., "Pharmaceutical Salts: A Summary on Doses of Salt Formers from the Orange Book," European Journal of Pharmaceutical Sciences, vol. 49, p. 614-623, (2013).
Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).
Satlin, et al., "ITI-007 (Lumateperone) for the Treatment of Agitation in Patients with Dementia, including Alzheimer's Disease," Poster P2-032, Alzheimer's Assoc. International Conference 2018 (2018).
Snyder et al., "Functional profile of a novel modulator of serotonin, dopamine, and glutamate neurotransmission", Psychopharmacology, Published online Aug. 2014, DOI 10.1007/s00213-014-3704-1.
Steffen Paulekuhn et al., "Trends in Active Pharmaceutical Ingredient Salt Selection based on Analysis of the Orange Book Database," J Med Chem., vol. 50, p. 6665-6672, (2007).
Vanover et al., Abstracts of the 13th International Congress on Schizophrenia (ICOSR) (Apr. 2-6, 2011), Schizophrenia Bull. 37 Suppl. 1., p. 325 (Mar. 2011).

(56) References Cited

OTHER PUBLICATIONS

Vanover, et al., "Dopamine D2 receptor occupancy of lumateperone (ITI-007): a Positron Emission Tomography Study in patients with schizophrenia," *Neuropsychopharmacology* 44:598-605, (2019).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, K., et al., "ITI-007: A Novel Therapy for the Treatment of Schizophrenia and Related Psychoses," International Clinical Psychoparamcology, vol. 26, e56, 1 page, (2011).
Vanover, et al., "Lumateperone (ITI-007): A Novel Investigational Agent with Broad Therapeutic Potential Across Multiple Neuropsychiatric Disorders," *European Neuropsychopharmacology*, 27:S660-61 (2017) (Summary of ECNP Poster P.1.g.038).
Vyas, P., et al., "An Evaluation of Lumateperone Tosylate for the Treatment of Schizophrenia," Expert Opinion on Pharmacotherapy, vol. 21, No. 2, pp. 139-145, (2020); https://doi.org/10.1080/14656566. 2019.1695778.
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Avendaño, C., et al., "The Problem of the Existence of C(Ar)-H . . . N Intramolecular Hydrogen Bonds in a Family of 9-Azaphenyl-9H-carbazoles," J. Chem. Soc. Perkin. Trans., 2: 1547-1555 (1993).
Beletskaya, I., et al., "Pd- and Cu-catalyzed selective Arylation of Benzotriazole," Tetrahedron Letters, 39: 5617-5620 (1998).
Berger, J., et al., "Synthesis of Some Conformationally Restricted Analogues of Fentanyl," Journal of Medicinal Chemistry, 20(4): 600-602 (1977).
Boger, D., et al., "Inverse Electron Demand Diels-Alder Reactions of Heterocyclic Aza Dienes. Studies on the Total Synthesis of Lavendamycin: Investigative Studies on the Preparation of the CDE B-Carboline Ring System and AB Quinoline-5, 8-quinone Ring System," J. Org. Chem., 50: 5782-5789 (1985).
Bowman, W.R., et al., "Copper(1) Catalysed Aromatic Nucleophilic Substitution: A Mechanistic and Synthetic Comparison with the SRN1 Reaction," Tetrahedron Letters, 25(50): 5821-5824 (1984).
Bowman, W.R., et al., "Intramolecular Aromatic Substitution (SRN1) Reactions, Use of Entrainment for the Preparation of Benzothiazoles," Tetrahedron Letters, 23(48): 5093-5096 (1982).
Bowman, W.R., et al., "Synthesis of 1H-quinazoline-4-ones using intramolecular aromatic nucleophilic substitution," ARKIVOC, x: 434-442 (2003).
Crawford, K., et al., "Copper-catalyzed amidations of bromo substituted furans and thiophenes," Tetrahedron Letters, 43: 7365-7368 (2002).
Evindar, G., et al., "Copper- and Palladium-Catalyzed Intramolecular Aryl Guanidinylation: An Efficient Method for the Synthesis of 2- Aminobenzimidazoles," Organic Letters, 5(2): 133-136 (2003).
Ezquerra, J., et al., "Efficient Reagents for the Synthesis of 5-, 7-, and 5,7-Substituted Indoles Starting from Aromatic Amines: Scope and Limitations," J. Org. Chem., 61: 5804-5812 (1996).
Fee, W.W., et al., "Copper (II)-Promoted Solvolyses of Nickel(II) Complexes III. Tetradentate Schiff Base Ligands Containing Various Diamine Segments," Aust. J. Chem., 26: 1475-1485 (1973).
Ferreira, I., et al., "Novel synthetic routes to thienocarbazoles via palladium or copper catalyzed amination or amidation of arylhalides and intramolecular cyclizaiton," Tetrahedron, 58: 7943-7949 (2002).
Finet, J., et al., "Recent Advances in Ullmann Reaction: Copper(II) Diacetate Catalysed N-, O- and S-Arylation Involving Polycoordinate Heteroatomic Derivatives," Current Organic Chemistry, 6: 597-626 (2002).
Goodbrand, H.B., et al., "Ligand-Accelerated Catalysis of the Ullmann Condensation: Application to Hole Conducting Triarylamines," J. Org. Chem., 64: 670-674 (1999).

Hamann, B., et al., "Systematic Variation of Bidentate Ligands Used in Aryl Halide Amination. Unexpected Effects of Steric, Electronic, and Geometric Perturbations," J. Am. Chem. Soc., 120: 3694-3703 (1998).
Hartwig, J.F., "Palladium-Catalyzed Amination of Aryl Halides: Mechanism and Rational Catalyst Design," Synlett, 329-340 (1996).
Hassan, J., et al., "Aryl-aryl bond formation one century after the discovery of the ullmann reaction," Chem. Rev., 102: 1359-1469 (2002).
Ito, T., et al., "Studies of Organic Catalytic Reactions. VI. The Function of Pyridine and Copper in the Rosenmund-von Braun reaction," Bulletin of the Chemical Society of Japan, 41: 419-423 (1968).
Ji, J., "Selective Amination of Polyhalpyridines Catalyzed by a Palladium-Xantphos Complex," Organic Letters, 5(24): 4611-4614 (2003).
Kametani, T., et al., "A Novel Synthesis of Indole Derivatives," Heterocycles, 14(3): 277-280 (1980).
Kang, S.K., "Copper-catalyzed N-Arylation of Aryl Iodides with Benzamides or Nitrogen Heterocycles in the Presence of Ethylenediamine," Synlett, 3: 427-430 (2002).
Kiyomori, A., et al., "An Efficient Copper-Catalyzed Coupling of Aryl Halides with Imidazoles," Tetrahedron Letters, 40: 2657-2660 (1999).
Klapars, A., et al., "A General and Efficient Copper Catalyst for the Amidation of Aryl Halides," J. Am. Chem. Soc., 124: 7421-7428 (2002).
Klapars, A., et al., "A General and Efficient Copper Catalyst for the Amidation of Aryl Halides and the N-Arylation of Nitrogen Heterocycles," J. Am. Chem. Soc., 123: 7727-7729 (2001).
Kondratov, S.A., et al., "Nucleophilic Substitution in the Aromatic Series. LV. Reaction of o-Nitrochlorobenzene with Ammonia in the Presence of Copper Compounds," Zhurnal Organidreskoi Khimii, 51(11): 2387-2390 (1979).
Kwong, F., et al., "Mild and Efficient Copper-Catalyzed Amination of Aryl Bromides with Primary Alkylamines," Organic Letters, 5(6): 793-796 (2003).
Lee, T., et al., "Novel, Highly Potent, Selective 5-HT2A/D2 Receptor Antagonists as Potential Atypical Antipsychotics," Bioorganic & Medicinal Chemistry Letters, 13: 767-770 (2003).
Louie, J., et al., "Palladium-Catalyzed Synthesis of Arylamines from Aryl Halides. Mechanistic Studies Lead to Coupling in the Absence of Tin Reagents," Tetrahedron Letters, 36(21): 3609-3612 (1995).
Marcoux, J., et al., "A General Copper-Catalyzed Synthesis of Diaryl Ethers," J. Am. Chem. Soc., 119: 10539-10540 (1997).
Mulrooney, C.A., "Recent Developments in Copper-Catalyzed N-Arylation with Aryl Halides," Essay—University of Pennsylvania (2004).
Sadighi, J., et al., "A Highly Active Palladium Catalyst System for the Arylation of Anilines," Tetrahedron Letters, 39: 5327-5330 (1998).
Sugahara, M., et al., "A Facile Copper-Catalyzed Ullmann Condensation: N-Arylation of Heterocyclic Compounds Containing an -NHCO-Moiety," Chem. Pharm. Bull., 45(4): 719-721 (1997).
Wagaw, S., et al., "A Palladium-Catalyzed Method for the Preparation of Indoles via the Fischer Indole Synthesis," Journal of the American Chemical Society, 121(44): 10251-10263 (1999).
Wolfe, J., et al., "An Improved Catalyst System for Aromatic Carbon-Nitrogen Bond Formation: The Possible Involvement of Bis(Phosphine) Palladium Complexes as Key Intermediates," J. Am. Chem. Soc., 118: 7215- 7216 (1996).
Wolfe, J., et al., "Intramolecular Palladium-Catalyzed Aryl Amination and Aryl Amidation," Tetrahedron, 52(21): 7525-7546 (1996).
Wolter, M., et al., "Synthesis of N-Aryl Hydrazides by Copper-Catalyzed Coupling of Hydrazides with Aryl Iodides," Organic Letters, 3(23): 3803-3805 (2001).
Yamada, K., et al., "A Mild Copper-mediated Intramolecular Amination of Aryl Halides," Synlett, 2: 231-234 (2002).
Yang, B., et al., "The development of efficient protocols for the palladium-catalyzed cyclization reactions of secondary amides and carbamates," Organic Letters, 1(1): 35-37 (1999).

(56) References Cited

OTHER PUBLICATIONS

Zhang, Z., et al., "Highly efficient copper-catalyzed N-arylation of alkylamines with aryl iodides using phosphoramidite as ligand," Catalysis Communications, 6: 784-787 (2005).

* cited by examiner

LUMATEPERONE BIS-TOSYLATE SALTS AND CRYSTALS AND METHODS FOR MANUFACTURE THEREOF

CROSS-REFERENCE TO RELATED APPLICATIONS

This application is a continuation of application Ser. No. 16/714,139, filed on Dec. 13, 2019, which is a continuation application filed under 35 U.S.C. § 111 (a) of International Application No. PCT/US2019/035845 filed on Jun. 6, 2019, which claims benefit to and priority from U.S. Provisional Application No. 62/681,534, filed on Jun. 6, 2018, the contents of each of which are hereby incorporated by reference in their entireties.

FIELD

This disclosure relates to certain salts and crystal forms of a substituted heterocycle fused gamma-carboline, the manufacture thereof, pharmaceutical compositions thereof, and use thereof, e.g., in the treatment of diseases or abnormal conditions involving or mediated by the 5-$HT_{2A}$ receptor, serotonin transporter (SERT), and/or dopamine $D_1/D_2$ receptor signaling pathways.

BACKGROUND 1-(4-flurophenyl)-4-6bR, 10aS)-3-methyl-2,3,6b,9,10,10a-hexahydro-1H,7H-pyrido[3',4':4,5]pyrrolo[1,2,3-de]quinoxalin-8-yl)-butan-1-one (sometimes referred to as 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, and also known as Lumateperone or as ITI-007), has the following structure:

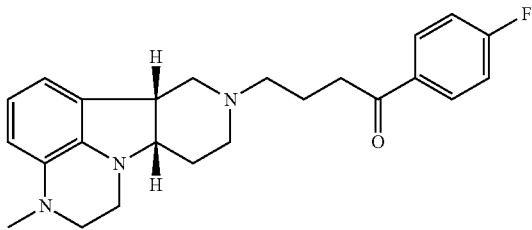 [SMILES: CN1CCN2c3c(cccc31)[C@@H]1CN(CCCC(=O)c3ccc(F)cc3)CC[C@@H]12]

ITI-007 is a potent 5-$HT_{2A}$ receptor ligand ($K_i$=0.5 nM) with a strong affinity for the dopamine (DA) D2 receptor ($K_i$=32 nM) and the serotonin transporter (SERT) ($K_i$=62 nM), but negligible binding to receptors associated with cognitive and metabolic side effects of antipsychotic drugs (e.g., H1 histaminergic, 5-$HT_{2C}$, and muscarinic). ITI-007 is also active at the dopamine D1 receptor ($K_i$=52 nM), and indirectly via this interaction, ITI-007 has been found to result in enhanced NMDA and AMPA signaling in the brain, especially in the medial prefrontal cortex (mPFC). ITI-007 is currently in clinical trials, e.g., for the treatment of schizophrenia, depression, and other psychological disorders. While ITI-007 is a promising drug, its production and formulation present challenges. In free base form, ITI-007 is an oily, sticky solid, with poor aqueous solubility. Making salts of the compound has proven to be unusually difficult. A hydrochloride salt form of ITI-007 was disclosed in U.S. Pat. No. 7,183,282, but this particular salt form was hygroscopic and showed poor stability. It was obtained by precipitation from diethyl ether. A toluenesulfonic acid addition salt (tosylate) of ITI-007 was finally identified and described in WO 2009/114181 and US 2011/0112105 (U.S. Pat. No. 8,648,077).

There is a need for alternative stable and pharmaceutically acceptable salts and polymorphs of ITI-007.

SUMMARY

In an effort to find new salts and polymorphs of ITI-007, an extensive salt screen was undertaken. ITI-007 does not readily form salts with other common, pharmaceutically acceptable acids, despite the good solubility of the free base in a variety of organic solvents. Initially, a toluenesulfonic acid addition salt (tosylate) was prepared, as described in WO 2009/114181 and US 2011/0112105, but no other stable salts were found. Finally, a major salt screen was carried out, wherein the free base compound was studied in different solvent systems and under different conditions, and then systematically screened using a selection of over 100 acids under different conditions and with different solvent, co-solvent and anti-solvent systems, to identify new possible salt forms. Following extensive screening and experimentation, a new bis-tosylate salt polymorph was discovered. This new bistosylate salt form is crystalline and stable.

The present disclosure thus provides a new bis-tosylate salt form of ITI-007, which is especially advantageous for use in the preparation of galenic formulations, together with methods of making and using the same. This disclosure shows that this new bis-tosylate salt form of ITI-007 can be prepared under various conditions, including from the free base form of ITI-007, as well as from the mono-tosylate salt form of ITI-007.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

BRIEF DESCRIPTION OF THE DRAWINGS

The present invention will become more fully understood from the detailed description and the accompanying drawings.

DETAILED DESCRIPTION

Figure 1:
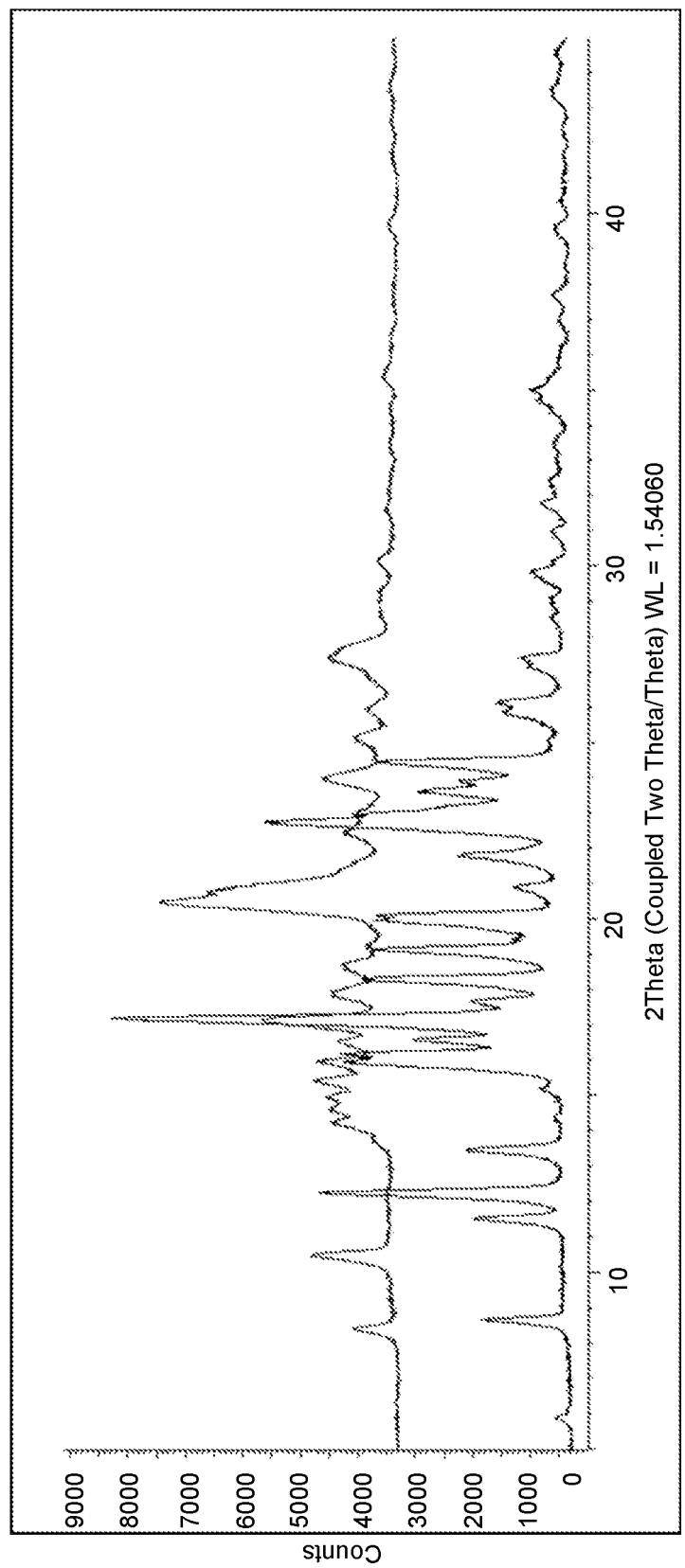
FIG. 1 depicts overlaid X-ray powder diffraction (XRPD) patterns for the ITI-007 bis-tosylate salt crystal obtained from Example 1 (from a 1:1 molar mixture of ITI-007 free base and toluenesulfonic acid) (upper curve), with reference to the known XRPD pattern for ITI-007 mono-tosylate salt crystal (lower curve).

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

In a first embodiment, the invention provides 1-(4-fluorophenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) in stable bis-tosylate salt form (Salt 1). In additional embodiments, the invention further provides the following:

1.1. Salt 1, wherein the salt is in solid form.
1.2. Salt 1 or 1.1, wherein the salt is in crystalline form, e.g., dry crystalline form.
1.3. Salt 1.2, wherein the salt is in a homogeneous crystal form, e.g., free or substantially free of other forms of ITI-007, e.g., free or substantially free, e.g., less than 10 wt. %, preferably less than about 5 wt. %, more preferably less than about 2 wt. %, still preferably less than about 1 wt. %, still preferably less than about 0.1%, most preferably less than about 0.01 wt. %, of any amorphous forms.
1.4. Any foregoing form of Salt 1, wherein the salt is in crystalline form, crystallized from 2-butanone solvent.
1.5. Any foregoing form of Salt 1, wherein the salt is a solvate, e.g., a 2-butanone solvate.
1.6. Any foregoing form of Salt 1, wherein the salt is not a solvate.
1.7. Any foregoing form of Salt 1, wherein the salt is a hydrate.
1.8. Any foregoing form of Salt 1, wherein the salt is not a hydrate.
1.9. Any foregoing form of Salt 1, wherein the salt is formed by combining free ITI-007 free base and toluenesulfonic acid in a molar ratio from 1:1 to 1:3, e.g., a molar ratio from 1:1 to 1:2.2, or from 1:1 to 1:2, or from 1:1 to 1:1.5, or a molar ratio of about 1:1, or about 1:1.5, or about 1:2, or about 1:2.2.
1.10. Any foregoing form of Salt 1, wherein the salt is formed from a slurry of ITI-007 free base and toluenesulfonic acid in 2-butanone solvent.
1.11. Any foregoing form of Salt 1, wherein a DSC/TGA analysis of the salt shows one endothermic event at about 184° C., and one exothermic event at about 258° C., e.g. wherein a DSC/TGA analysis shows the first endothermic event at about $T_{onset}$=178° C., $T_{peak}$=184° C. and $\Delta E$=−88 J/g, and the second exothermic event at about $T_{onset}$=242° C., $T_{peak}$=258° C. and $\Delta E$=122 J/g, for example, wherein the first endothermic event is a melt and the second exothermic event is a recrystallization.
1.12. Any foregoing form of Salt 1, wherein the salt is in the form of a crystal having an X-ray powder diffraction pattern corresponding to the d-spacing and/or angle (2-theta) values of the following table, for example, wherein the pattern comprises at least five, or at least six, or at least seven, or at least eight of said values, e.g., taking into account potential variations due to sample purity and instrument variation, for example 2θ shifts due to variation in X-ray wavelength, e.g., wherein the X-ray powder diffraction pattern is generated using an X-ray diffractometer with a copper anode and a nickel filter, e.g., comprising at least those peaks having a relative intensity of at least 0.4, at least 0.5, or at least 0.6, or comprising peaks 1, 2, 6, 7, 8, and 9:

| XRPD (Cu anode, Ni filter) for Bis-tosylate Salt Crystal Polymorph 1 | | | |
|---|---|---|---|
| # | Angle | d Value | Rel. Intensity |
| 1 | 6.347 | 13.9139 | 1.70% |
| 2 | 8.389 | 10.53127 | 18.20% |
| 3 | 10.453 | 8.45646 | 36.00% |
| 4 | 13.794 | 6.41449 | 6.60% |
| 5 | 14.26 | 6.20595 | 24.30% |
| 6 | 14.661 | 6.03727 | 25.20% |
| 7 | 14.916 | 5.93459 | 25.20% |
| 8 | 15.397 | 5.75029 | 31.10% |
| 9 | 15.925 | 5.56057 | 27.10% |
| 10 | 16.51 | 5.36504 | 18.60% |
| 11 | 17.106 | 5.1793 | 54.00% |
| 12 | 17.895 | 4.95287 | 21.80% |
| 13 | 18.65 | 4.75399 | 14.70% |
| 14 | 19.198 | 4.61939 | 3.10% |
| 15 | 20.488 | 4.33151 | 100.00% |
| 16 | 20.67 | 4.29368 | 75.70% |
| 17 | 20.857 | 4.25564 | 68.10% |
| 18 | 22.468 | 3.95398 | 15.00% |
| 19 | 22.9 | 3.88029 | 11.80% |
| 20 | 23.973 | 3.709 | 24.60% |
| 21 | 25.114 | 3.54305 | 12.80% |
| 22 | 25.919 | 3.43479 | 7.90% |
| 23 | 27.032 | 3.29588 | 10.80% |
| 24 | 27.416 | 3.25062 | 27.80% |
| 25 | 28.738 | 3.10393 | 3.90% |
| 26 | 29.14 | 3.06208 | 3.40% |
| 27 | 30.128 | 2.96386 | 6.10% |
| 28 | 31.645 | 2.82511 | 3.00% |
| 29 | 33.432 | 2.67815 | 1.50% |
| 30 | 35.412 | 2.53276 | 5.30% |
| 31 | 36.475 | 2.46136 | 2.30% |
| 32 | 39.667 | 2.27035 | 3.90% |
| 33 | 42.624 | 2.11941 | 2.50% |
| 34 | 43.595 | 2.07446 | 1.80% |

1.13. Any foregoing form of Salt 1, wherein the salt is in the form of a crystal having an X-ray powder diffraction pattern corresponding to FIG. 1 (upper curve), e.g., taking into account potential variations due to sample purity and instrument variation, for example 2θ shifts due to variation in X-ray wavelength, e.g., an X-ray powder diffraction pattern corresponding to FIG. 1 generated using an X-ray diffractometer with a copper anode and a nickel filter.

1.14. Any foregoing form of Salt 1, wherein the salt is in the form of a crystal having an X-ray powder diffraction pattern having at least 5, or at least 6, or at least 7, or at least 8, peaks having angle (2-theta) values selected from the group consisting of about 6.35, 8.39, 10.45, 13.79, 14.26, 14.66, 14.92, 15.40, 15.93, 16.51, 17.11, 17.90, 18.65, 19.20, 20.49, 20.67, 20.86, 22.47, 22.90, 23.97, 25.11, 25.92, 27.03, 27.42, 28.74, 29.14, 30.13, 31.65, 33.43, 35.41, 36.48, 39.67, 42.62, and 43.56, taking into account potential variations due to sample purity and instrument variation, e.g., wherein the X-ray powder diffraction pattern is generated using an X-ray diffractometer with a copper anode and a nickel filter.

1.15. Any foregoing form of Salt 1, in the form of a crystal having an X-ray powder diffraction pattern having at least 5, or at least 6, or at least 7, or at least 8, peaks having d-spacing values selected from the group consisting of about 13.91, 10.53, 8.46, 6.42, 6.21, 6.04, 5.93, 5.75, 5.56, 5.37, 5.18, 4.95, 4.75, 4.62, 4.33, 4.29, 4.26, 3.95, 3.88, 3.71, 3.54, 3.44, 3.30, 3.25, 3.10, 3.06, 2.96, 2.83, 2.68, 2.53, 2.46, 2.27, 2.12, and 2.07, taking into account potential variations due to sample purity and instrument variation, wherein the X-ray powder diffraction pattern is generated using an X-ray diffractometer with a copper anode and a nickel filter.

1.16. Any foregoing form of Salt 1, wherein the salt is in the form of a crystal having an X-ray powder diffraction pattern having at least 5, or at least 6, or at least 7, or at least 8, peaks having angle (2-theta) values and/or d-spacing values as provided in Salts 1.14 and/or 1.15.

1.17. Any foregoing form of Salt, wherein the salt is in the form of a crystal having an X-ray powder diffraction pattern having at least a peak of 25% relative intensity at an angle (2-theta) value of 10.2-10.5 (e.g., 10.3-10.5, or about 10.3, or about 10.4 or about 10.45, or about 10.5), optionally, wherein said peak has a relative intensity of at least 30% or at least 40% or at least 50%, or about 25% or about 30%, or about 35%.

1.18. Any foregoing form of Salt 1, wherein the salt is in the form of a crystal having an X-ray powder diffraction powder having relative angle (2-theta) values as provided in the table of embodiment 1.12, wherein the values are shifted by up to +/−0.2 degrees, e.g., wherein the values are substantially uniformly shifted by up to +/−0.2 degrees.

1.19. Any foregoing form of Salt 1, wherein the salt is in the form of a crystal having an X-ray diffraction pattern as shown, or substantially as shown, in the upper curve of FIG. 1.

1.20. Any foregoing form of Salt 1, wherein the salt is in the form of a crystal having a DSC/TGA thermogram as shown, or substantially as shown, in FIG. 2.

1.21. Any foregoing form of Salt 1, wherein the salt has a proton NMR spectrum as shown, or substantially as shown, in FIG. 3.

1.22. Any foregoing form of Salt 1, wherein the salt has a proton NMR spectrum indicating the presence of about two toluenesulfonic acid moieties per ITI-007 base moiety, e.g., as demonstrated by the NMR proton peaks at (i.e., the multiplets centered at) about 7.11 ppm, 7.36 ppm, 7.49 ppm and 8.03 ppm at about an integral ratio of 4:2:4:2 (when the spectrum is taken at 400 MHz in DMSO-d6 solvent).

1.23. Any foregoing form of Salt 1, wherein the salt has an FTIR spectrum as shown, or substantially as shown, in FIG. 4.

1.24. Any foregoing form of Salt 1, wherein the salt contains less than 10 wt % of any other ITI-007 tosylate salt form (e.g., mono-tosylate salt or tri-tosylate salt), e.g., less than 5%, or less than 3%, or less than 2%, or less than 1%, or less than 0.5%, by weight of Salt 1.

1.25. Any foregoing form of Salt 1, wherein the salt contains less than 10 wt % of ITI-007 free base form, e.g., less than 5%, or less than 3%, or less than 2%, or less than 1%, or less than 0.5%, by weight of Salt 1.

1.26. Any foregoing form of Salt 1, wherein the ITI-007 is deuterated, e.g., wherein the deuterium:protium ratio at one or more specified positions in the molecule is significantly higher, e.g., at least 2×, for example at least 10× higher, than the natural isotope ratios or the isotope ratios at other positions in the molecule; for example, any foregoing form of Salt 1 wherein the —$CH_2$— adjacent to the methylated nitrogen moiety and/or adjacent to the carbonyl moiety of ITI-007 is deuterated, e.g., is in the form of —CHD— or —$CD_2$— at levels which are significantly higher than the natural deuterium:protium isotope ratio or the deuterium:protium isotope ratio at other positions in the molecule, and/or wherein the methyl group is deuterated, e.g., is $CD_3$—, e.g., at levels which are significantly higher than the natural deuterium:protium isotope ratio or the deuterium:protium isotope ratio at other positions in the molecule, e.g., as described in WO 2015/154025 (and U.S. Pat. Pub. 2017/0183350) or as described in WO 2017/165843 (equivalent to U.S. Applic. Ser. No. 16/088,397), the contents of each of which are incorporated herein by reference.

1.27. Any foregoing form of Salt 1, wherein the salt exhibits any combination of characteristics as described in 1.1-1.26.

In another embodiment, the invention provides a process (Process 1) for the production of Salt 1, comprising (a) reacting 1-(4-fluorophenyl)-4-((6bR,10aS)-3-methyl-2,3,6b,9,10,10a-hexahydro-1H,7H-pyrido[3',4':4,5] pyrrolo[1,2,3-de]quinoxalin-8-yl)-butan-1-one (ITI-007) free base with toluenesulfonic acid, e.g., together with an organic solvent (e.g., comprising 2-butanone), for example, wherein the ITI-007 free base and toluenesulfonic acid are in a molar ratio from 1:1 to 1:3, e.g., a molar ratio from 1:1 to 1:2.2, or from 1:1 to 1:2, or from 1:1 to 1:1.5, or a molar ratio of about 1:1, or about 1:1.5, or about 1:2, or about 1:2.2; and (b) recovering the salt thus formed, e.g., recovering Salt 1 or any of Salts 1.1-1.27.

In another embodiment of Process 1, the reaction step (a) comprises dissolving or suspending the ITI-007 free base in an organic solvent, e.g., 2-butanone, and adding thereto the toluenesulfonic acid. In another embodiment of Process 1, the reaction step (a) comprises combining the ITI-007 free base with the toluenesulfonic acid and adding thereto an organic solvent, e.g., 2-butanone.

In some embodiments of Process 1, the process step (a) is carried out as a batch process, and in other embodiments the process step (a) is carried out as a continuous (flow) process.

In another embodiment, the invention provides a pharmaceutical composition comprising Salt 1, or any of Salts 11-1.27, as active ingredient, in combination or association with a pharmaceutically acceptable diluent or carrier.

In another embodiment, the invention provides a pharmaceutical composition comprising Salt 1, or any of Salts 1.1-1.27, as active ingredient, in combination or association with a pharmaceutically acceptable diluent or carrier, wherein the salt is predominantly, or is entirely or substantially entirely, in dry crystalline form.

In a particular embodiment, the invention provides a pharmaceutical composition comprising Salt 1, or any of Salts 1.1-1.27, as active ingredient, in combination or association with a pharmaceutically acceptable diluent or carrier, wherein the composition is in the form of an injectable depot, e.g., to provide extended release of ITI-007.

In another embodiment, the invention provides a pharmaceutical composition (Composition 2) comprising:

(1) (a) 1-(4-fluorophenyl)-4-((6bR,10aS)-3-methyl-2,3, 6b,9,10,10a-hexahydro-1H,7H-pyrido[3 ',4':4,5]pyrrolo[1,2,3-de]quinoxalin-8-yl)-butan-1-one (ITI-007) free base or (b) an acid addition salt of 1-(4-fluorophenyl)-446bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) free base, and (2) at least 1 molar equivalent of toluenesulfonic acid based on the amount of 1-(4-fluorophenyl)-4,4(6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) present. Optionally the acid addition salt of ITI-007 in part (1)(b) is a hydrochloride salt of ITI-007.

In another embodiment, the invention provides a method of making Composition 2 comprising the steps of:

(1) Combining either (a) 1-(4-fluorophenyl)-4-((6bR,10aS)-3-methyl-2,3,6b,9,10,10a-hexahydro-1H,7H-pyrido[3',4,4,5]pyrrolo[1,2,3-de]quinoxalin-8-yl)-butan-1-one (ITI-007) free base or (b) an acid addition salt of 1-(4-fluorophenyl)-4-((6bR,10aS)-3-methyl-2,3,6b,9,10,10a-hexahydro-1H, 7H-pyrido[3',4,5]pyrrolo[1,2,3-de]quinoxalin-8-yl)-butan-1-one (ITI-007) free base, with (2) at least 1 molar equivalent of toluenesulfonic acid based on the amount of 1-(4-fluorophenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (ITI-007) present, and (3) mixing the components with at least one pharmaceutically acceptable diluent or carrier to form the Composition.

In another embodiment, the invention provides Salt 1, or any of Salts 1.1-1.27, or a pharmaceutical composition comprising Salt 1, or any of Salts 1.1-1.27, for use in treating a disease or abnormal condition involving or mediated by the $5\text{-}HT_{2A}$ receptor, serotonin transporter (SERT), and/or dopamine $D_1/D_2$ receptor signaling pathways, e.g., a disorder selected from obesity, anorexia, bulimia, depression, anxiety, psychosis, schizophrenia, migraine, obsessive-compulsive disorder, sexual disorders, bipolar depression, attention deficit disorder, attention deficit hyperactivity disorder, sleep disorders, conditions associated with cephalic pain, social phobias, and/or dementia.

In another embodiment, the invention provides a method for the prophylaxis or treatment of a human suffering from a disease or abnormal condition involving or mediated by the $5\text{-}HT_{2A}$ receptor, serotonin transporter (SERT), and/or dopamine $D_1/D_2$ receptor signaling pathways, e.g., a disorder selected from obesity, anorexia, bulimia, depression, anxiety, psychosis, schizophrenia, migraine, obsessive-compulsive disorder, sexual disorders, bipolar depression, attention deficit disorder, attention deficit hyperactivity disorder, sleep disorders, conditions associated with cephalic pain, social phobias, and/or dementia, the method comprising administering to a patient in need thereof a therapeutically effective amount of Salt 1, or any of Salts 1.1-1.27.

EXAMPLES

The following equipment and methods are used to isolate and characterize the exemplified salt forms:

X-ray powder diffraction (XRPD): The X-ray powder diffraction studies are performed using a Bruker AXS D2 PHASER in Bragg-Brentano configuration, equipment #1549/#2353.

The equipment uses a Cu anode at 30 kV, 10 mA; sample stage standard rotating; monochromatization by a Kβ-filter (0.5% Ni). Slits: fixed divergence slits 1.0 mm)(=0.61°, primary axial Soller slit 2.5°, secondary axial Soller slit 2.5°. Detector: Linear detector LYNXEYE with receiving slit 5° detector opening. The standard sample holder (0.1 mm cavity in (510) silicon wafer) has a minimal contribution to the background signal. Measurement conditions: scan range 5-45° 2θ, sample rotation 5 rpm, 0.5 s/step, 0.010°/step, 3.0 mm detector slit; and all measuring conditions are logged in the instrument control file. As system suitability, corundum sample A26-B26-S (NIST standard) is measured daily. The software used for data collection is Diffrac.Commander v2.0.26. Data analysis is done using Diffrac.Eva v1.4. No background correction or smoothing is applied to the patterns.

Simultaneous thermogravimetry (TGA) and differential scanning calorimetry (DSC) or TGA/DSC analysis: The TGA/DSC studies are performed using a Mettler Toledo TGA/DSC1 Stare System, equipment #1547, auto-sampler equipped, using pin-holed Al-crucibles of 40 µl. Measurement conditions: 5 min 30.0° C., 30.0–350.0° C. with 10° C./min., $N_2$ flow of 40 ml/min. The software used for instrument control and data analysis is STARe v12.10.

Differential scanning calorimetry (DSC): The DSC studies are performed using a Mettler Toledo DSC1 STARe System, equipment #1564. The samples are made using Al crucibles (40 µl; pierced). Typically, 1 to 8 mg of sample is loaded onto a pre-weighed Al crucible and is kept at 30° C. for 5 minutes, after which it is heated at 10° C./min from 30° C. to 350° C. and kept at 350° C. for 1 minute. A nitrogen purge of 40 ml/min is maintained over the sample. As system suitability checks, Indium and Zinc are used as references. The software used for data collection and evaluation is STARe Software v12.10 build 5937. No corrections are applied to the thermogram.

Fourier transform infrared spectroscopy (FT-IR): The FT-IR studies are performed using a Thermo Scientific Nicolet iS50, equipment #2357. An attenuated total reflectance (ATR) technique is used with a beam splitter of KBr. Number of scans is 16 with a resolution of 4, from 400 $cm^{-1}$ to 4000 $cm^{-1}$. The software OMNIC version 9.2 is used for data collection and evaluation.

High performance liquid chromatography (HPLC): The high performance liquid chromatography analyses are performed on an LC-31, equipped with an Agilent 1100 series G1322A degasser equipment #1894, an Agilent 1100 series G1311A quaternary pump equipment #1895, an Agilent 1100 series G1313A ALS equipment #1896, an Agilent 1100 series G1318A column equipment #1897 and an Agilent 1100 series G1314A VWD equipment #1898/LC-34, equipped with an Agilent 1200 series G1379B degasser equipment #2254, an Agilent 1100 series G1311A quaternary pump equipment #2255, Agilent 1100 series G1367A WPALS equipment #1656, an Agilent 1100 series G1316A column equipment #2257 and an Agilent 1100 series G1315B DAD equipment #2258. Data is collected and evaluated using Agilent ChemStation for LC systems Rev. B.04.02[96]. Solutions are prepared as follows: Mobile phase A: Add 800 ml of MilliQ water to a 1 L volumetric flask. Add 1 ml of TFA and homogenize. Fill up to the mark with MilliQ. Mobile phase B: Add 800 ml of Acetonitrile to a 1 L volumetric flask. Add 1 ml of TFA and homogenize. Fill up to the mark with Acetonitrile; Diluent: 50/50 MeOH/ACN.

Proton Nuclear Magnetic Resonance (NMR): Samples are prepared in DMSO-d6 solvent, and spectra are collected on an Agilent Inova400 at room temperature, and at a frequency of 399.9 MHz, with a sweep width of 6398 Hz, and spin of 20 Hz.

Example 1: ITI-007 Bis-Tosylate Salt

Approximately one gram of ITI-007 free base and one molar equivalent of toluenesulfonic acid is combined and mixed with 2-butanone solvent (20 mL). The mixture is stirred at 500 rpm at room temperature for 25 hours. The mixture is then filtered and dried to give a white/brown solid. The solid is analyzed by XRPD, DSC/TGA, HPLC, FTIR and proton NMR. The solid is found to be soluble in methanol and acetic acid (>30 mg/mL), and sparingly soluble in dichloromethane (10-30 mg/mL).

XRPD analysis shows the obtained solid to be a crystalline solid. The XRPD pattern is shown in FIG. 1 (upper curve) with reference to the XRPD pattern obtained from a previously made ITI-007 mono-tosylate salt crystal (lower curve). The reference crystal was obtained from a 1:1 molar mixture of ITI-007 and toluenesulfonic acid using ethyl acetate or toluene as solvent. The results show clear differences in the XPRD pattern between the solid obtained by Example 1 and the reference ITI-007 mono-tosylate salt. One key distinguishing peak that is believed to signal formation of the bis-tosylate salt appears at an angle (2-theta) of about 10.45. The peaks for the compound of Example 1 are identified in tabular form in table 1:

TABLE 1

XRPD peak list for ITI-007 Bis-tosylate Salt of Example 1

| # | Angle | d Value | Rel. Intensity |
|---|-------|---------|----------------|
| 1 | 6.347 | 13.9139 | 1.70% |
| 2 | 8.389 | 10.53127 | 18.20% |
| 3 | 10.453 | 8.45646 | 36.00% |
| 4 | 13.794 | 6.41449 | 6.60% |
| 5 | 14.26 | 6.20595 | 24.30% |
| 6 | 14.661 | 6.03727 | 25.20% |
| 7 | 14.916 | 5.93459 | 25.20% |
| 8 | 15.397 | 5.75029 | 31.10% |
| 9 | 15.925 | 5.56057 | 27.10% |
| 10 | 16.51 | 5.36504 | 18.60% |
| 11 | 17.106 | 5.1793 | 54.00% |
| 12 | 17.895 | 4.95287 | 21.80% |
| 13 | 18.65 | 4.75399 | 14.70% |
| 14 | 19.198 | 4.61939 | 3.10% |
| 15 | 20.488 | 4.33151 | 100.00% |
| 16 | 20.67 | 4.29368 | 75.70% |
| 17 | 20.857 | 4.25564 | 68.10% |
| 18 | 22.468 | 3.95398 | 15.00% |
| 19 | 22.9 | 3.88029 | 11.80% |
| 20 | 23.973 | 3.709 | 24.60% |
| 21 | 25.114 | 3.54305 | 12.80% |
| 22 | 25.919 | 3.43479 | 7.90% |
| 23 | 27.032 | 3.29588 | 10.80% |
| 24 | 27.416 | 3.25062 | 27.80% |
| 25 | 28.738 | 3.10393 | 3.90% |
| 26 | 29.14 | 3.06208 | 3.40% |
| 27 | 30.128 | 2.96386 | 6.10% |
| 28 | 31.645 | 2.82511 | 3.00% |
| 29 | 33.432 | 2.67815 | 1.50% |
| 30 | 35.412 | 2.53276 | 5.30% |
| 31 | 36.475 | 2.46136 | 2.30% |
| 32 | 39.667 | 2.27035 | 3.90% |
| 33 | 42.624 | 2.11941 | 2.50% |
| 34 | 43.595 | 2.07446 | 1.80% |

Figure 2:
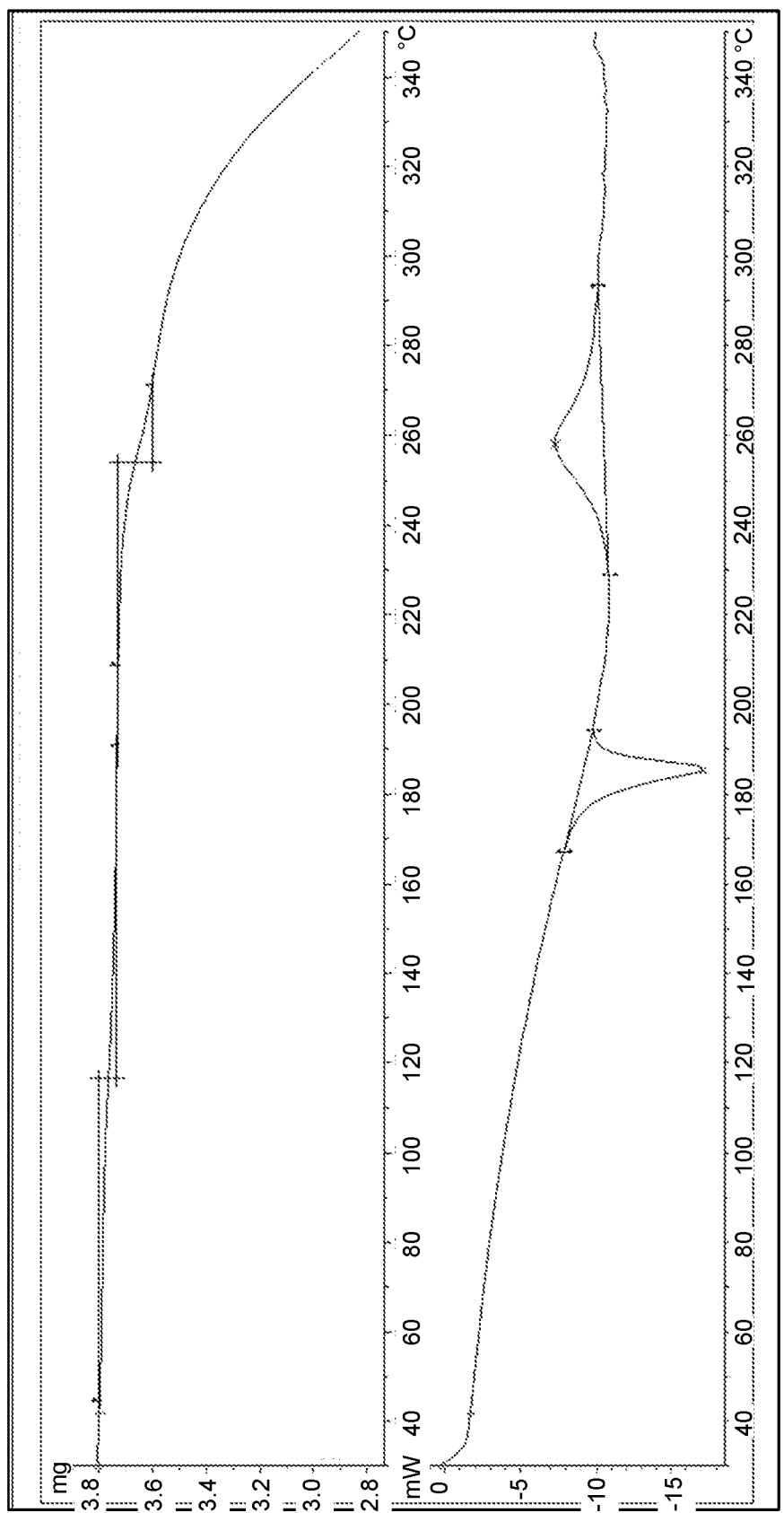
FIG. 2 depicts the TGA-DSC thermogram of the ITI-007 bis-tosylate salt crystal obtained from Example 1.

The DSC/TGA thermogram is shown in FIG. 2. DSC/TGA analysis shows one endothermic event at about 184° C., and one exothermic event at about 258° C. The first endothermic event occurs at about $T_{onset}$=178° C., with a $T_{peak}$=184° C. and a ΔE=−88 J/g. The second exothermic event occurs at about $T_{onset}$242° C., with a $T_{peak}$=258° C. and a ΔE=122 J/g. The endothermic event is a melt, while the exothermic event is a recrystallization. The TGA profile shows a mass loss of 1.7% from 40° C. to 190° C., and a mass loss of 3.4% from 210° C. to 270° C. It is noted that the recrystallization event occurs at a temperature about 25° C. lower than that previously observed for the reference ITI-007 mono-tosylate salt crystal.

LC-MS analysis shows a purity of 92 area % for the obtained solid.

Figure 3:
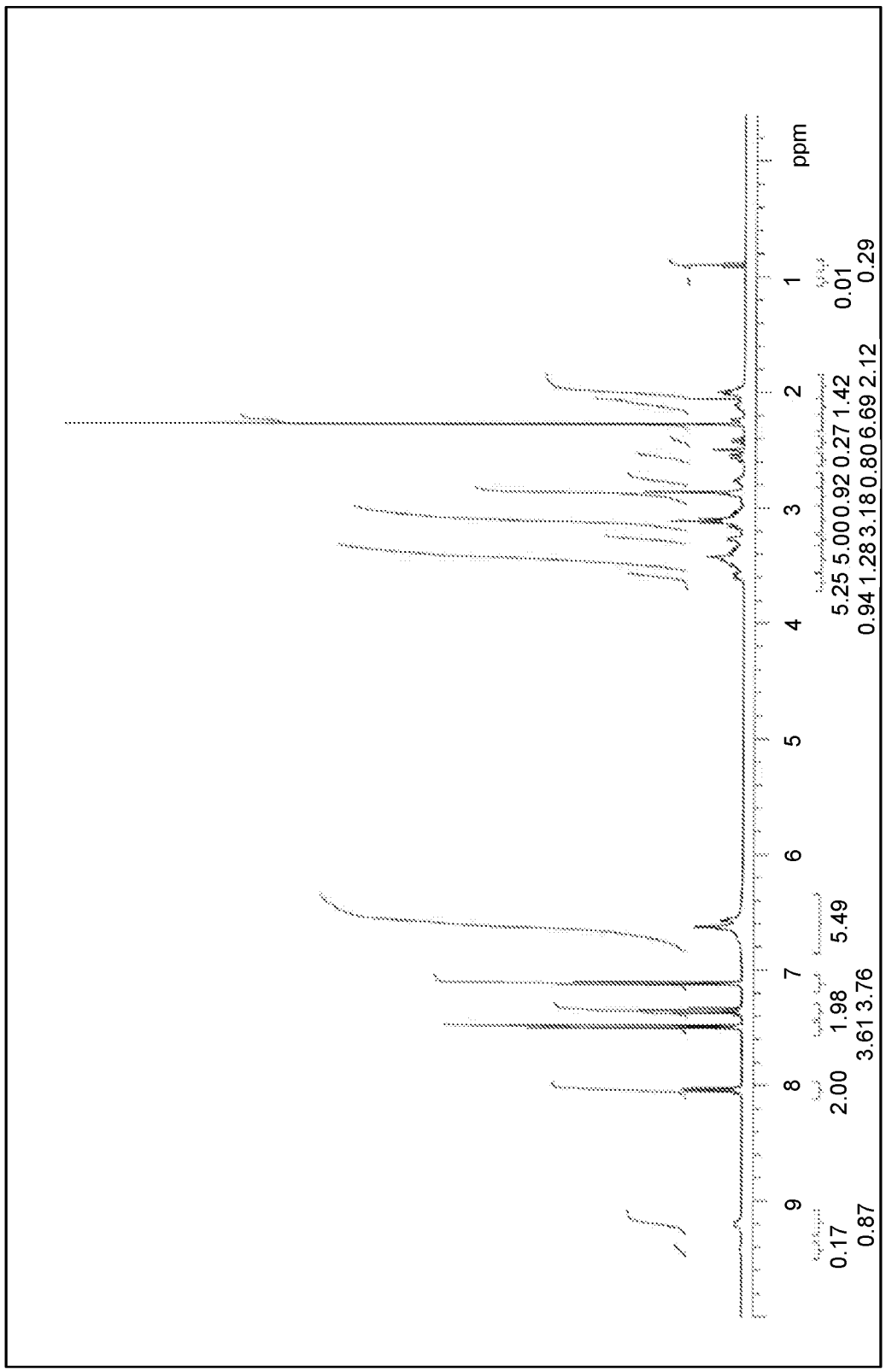
FIG. 3 depicts the 1H-NMR spectrum of the ITI-007 bis-tosylate salt crystal obtained from Example 1.

Proton NMR is shown in FIG. 3. Proton NMR analysis shows that the compound is the bis-tosylate salt of ITI-007. Specifically, the proton NMR spectrum shows the presence of about two toluenesulfonic acid moieties per ITI-007 base moiety. This is demonstrated by the NMR protons at about 7.11 ppm, 7.36 ppm, 7.49 ppm and 8.03 ppm, which are present at an integral ratio of about 4:2:4:2. The 7.11 and 7.49 ppm peaks represent protons from the aromatic tosylate ring of the toluene sulfonate moiety, while the 7.36 and 8.03 peaks represent protons from the aromatic 4-fluorophenyl ring of the ITI-007 moiety. The remaining aromatic peaks between 6.4 and 7.0 ppm represent the aromatic protons of the quinoxaline core of ITI-007 and their integral is consistent with one molar unit of ITI-007 free base. The alkyl peak at about 2.3 ppm represents the methyl group of the tosylate rings and its integral is also consistent with two molar units of toluenesulfonic acid.

Figure 4:
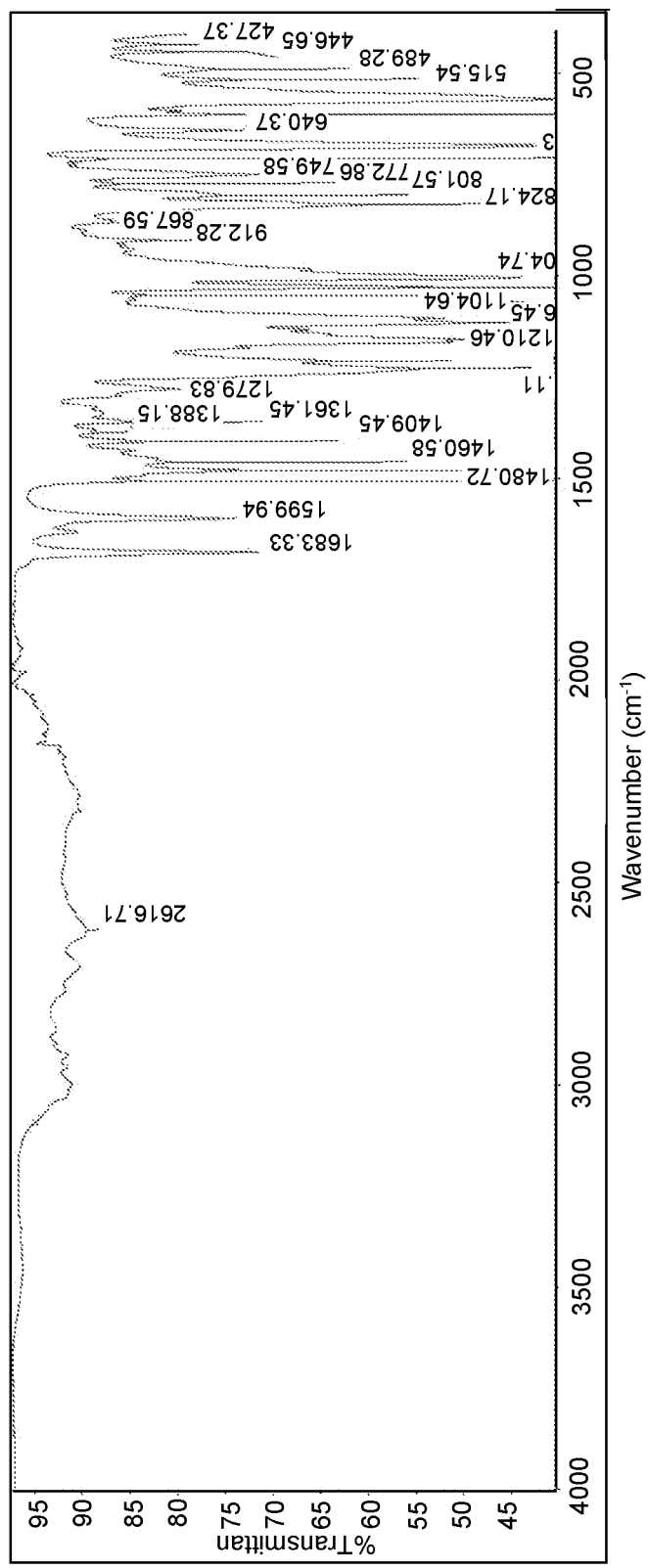
FIG. 4 depicts the FTIR spectrum of the ITI-007 bis-tosylate salt crystal obtained from Example 1.

The FTIR spectrum is shown in FIG. 4, and it is also consistent with a bis-tosylate structure of the salt.

Dynamic vapor sorption (DVS) analysis shows a stepwise sorption with a total mass uptake at 95 RH % of 2%. This salt is thus slightly hygroscopic. Analysis results are summarized in Table 2 below.

TABLE 2

Analytical results for ITI-007 Bis-tosylate Salt of Example 1

| Solvent | Appearance | DVS Hygroscopicity (%) | DSC ($T_{peak}$ ° C.) | DSC (ΔE J/s) | TGA: Mass loss (%) | HPLC purity (area %) |
|---------|------------|------------------------|----------------------|--------------|-------------------|---------------------|
| 2-Butanone | White/brown solid | 2 | 184 | −88 | 1.7 | 92 |
|  |  |  | 258 | +121 | 3.4 |  |

In direct comparison to the analytical data obtained on the mono-tosylate salt of Example 2, it is apparent that the salt of Example 1 is a distinct crystalline salt form comprising a 1:2 molar ratio of ITI-007 free base to toluene sulfonic acid. Without being bound by theory, it is believed that the lower solubility of ITI-007 free base in 2-butanone solvent, compared to other solvents, result in the effective concentration of free base being lower, and the effective ratio of free base to toluenesulfonic acid being higher. As a result, the bis-tosylate salt forms and unreacted free base remains in solution after filtration of the product.

Additional experiments demonstrate that at a 1:2 molar ratio of ITI-007 free base to toluenesulfonic acid in 2-butanone solvent, conducted substantially as described above, the solid collected after filtration is the same bis-tosylate salt as described above in high to quantitative yield.

Example 2: ITI-007 Mono-Tosylate Salt

Approximately one gram of ITI-007 free base and one-half molar equivalent of toluenesulfonic acid is added mixed with 2-butanone solvent (15 mL). The mixture is stirred at 500 rpm at room temperature for 25 hours. The mixture is then filtered and dried to give a white solid. The solid is analyzed by XRPD, DSC/TGA, HPLC, FTIR and proton NMR. The analysis demonstrates that this salt is a mono-tosylate salt of ITI-007 and it is distinctly different from the bis-tosylate salt obtained from Example 1.

Figure 5:
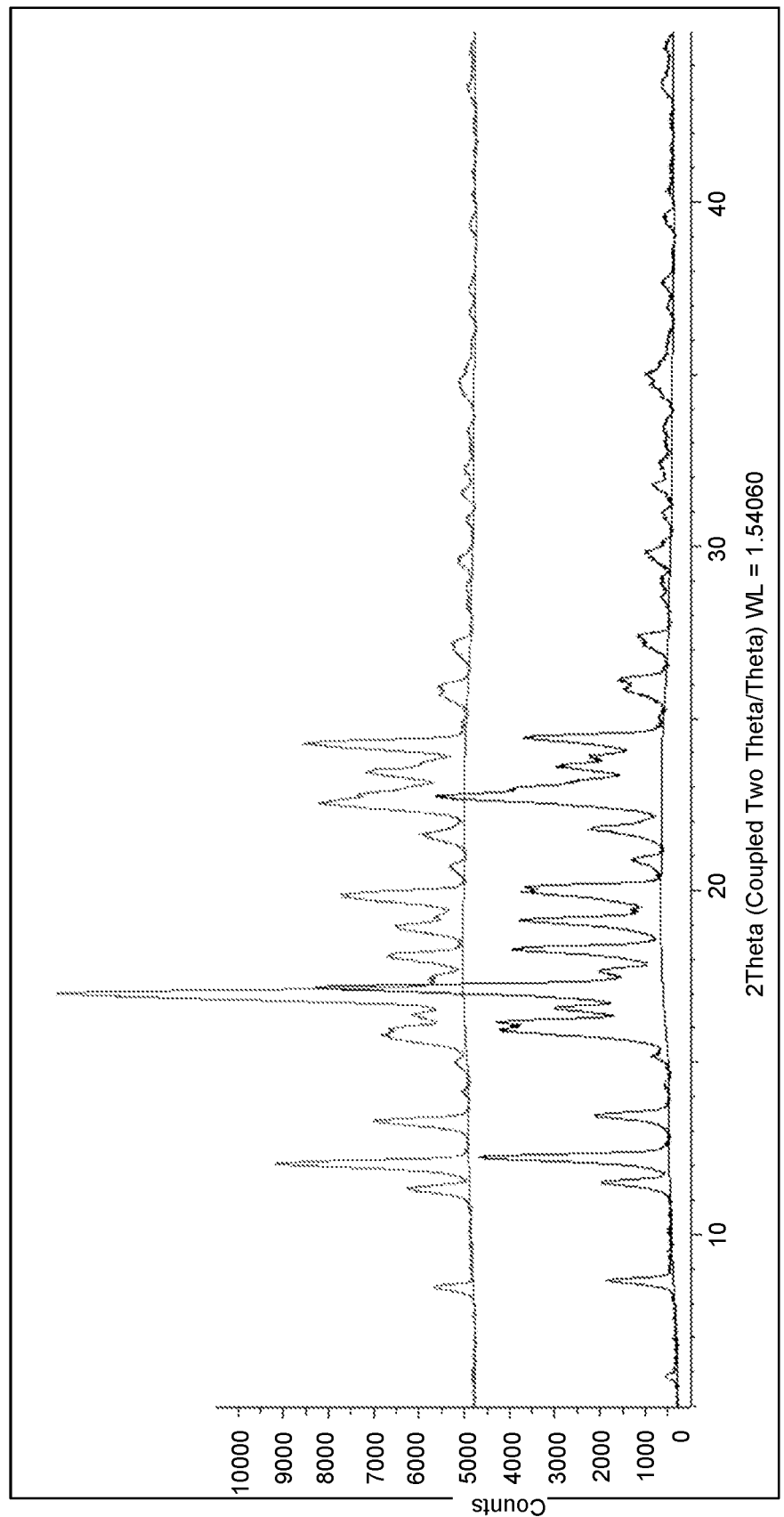
FIG. 5 depicts overlaid X-ray powder diffraction (XRPD) patterns for the ITI-007 mono-tosylate salt crystal obtained from Example 2 (from a 2:1 molar mixture of ITI-007 free base and toluenesulfonic acid) (upper curve), with reference to the known XRPD pattern for ITI-007 mono-tosylate salt crystal (lower curve).

XRPD analysis shows the obtained solid to be a crystalline solid. The XRPD pattern is shown in FIG. 5 (upper curve) with reference to the XRPD pattern obtained from a previously made ITI-007 mono-tosylate salt crystal (lower curve). The reference crystal was obtained from a 1:1 molar mixture of ITI-007 and toluenesulfonic acid using ethyl acetate or toluene as solvent. The results show substantially the same XPRD pattern between the solid obtained by Example 2 and the reference ITI-007 mono-tosylate salt. The peaks for the compound of Example 2 are identified in tabular form in table 3:

TABLE 3

XRPD peak list for ITI-007 Mono-tosylate Salt of Example 2

| # | Angle | d Value | Rel. Intensity |
|---|---|---|---|
| 1 | 8.463 | 10.43945 | 9.70% |
| 2 | 11.331 | 7.80275 | 15.20% |
| 3 | 12.059 | 7.33324 | 47.30% |
| 4 | 13.285 | 6.65902 | 23.70% |
| 5 | 14.142 | 6.25762 | 1.00% |
| 6 | 14.987 | 5.90646 | 3.20% |
| 7 | 15.802 | 5.6038 | 21.50% |
| 8 | 15.929 | 5.55918 | 18.40% |
| 9 | 16.381 | 5.40706 | 13.20% |
| 10 | 16.993 | 5.21366 | 100.00% |
| 11 | 17.432 | 5.08331 | 7.80% |
| 12 | 18.096 | 4.89827 | 18.90% |
| 13 | 18.938 | 4.68221 | 16.60% |
| 14 | 19.218 | 4.61464 | 6.30% |
| 15 | 19.854 | 4.46835 | 29.10% |
| 16 | 20.686 | 4.29037 | 4.00% |
| 17 | 21.612 | 4.10869 | 9.40% |
| 18 | 22.557 | 3.93865 | 35.70% |
| 19 | 22.757 | 3.90439 | 26.00% |
| 20 | 23.442 | 3.79192 | 24.90% |
| 21 | 23.642 | 3.7602 | 11.20% |
| 22 | 24.263 | 3.66543 | 39.40% |
| 23 | 25.727 | 3.46008 | 6.50% |
| 24 | 25.912 | 3.43574 | 7.40% |
| 25 | 27.162 | 3.28038 | 4.30% |
| 26 | 29.604 | 3.01515 | 3.30% |
| 27 | 30.804 | 2.90033 | 1.60% |
| 28 | 31.551 | 2.83332 | 3.10% |
| 29 | 32.265 | 2.77228 | 2.30% |
| 30 | 34.662 | 2.58583 | 3.60% |
| 31 | 36.82 | 2.43906 | 1.60% |
| 32 | 37.497 | 2.39657 | 1.60% |
| 33 | 39.386 | 2.28588 | 1.30% |

Figure 6:
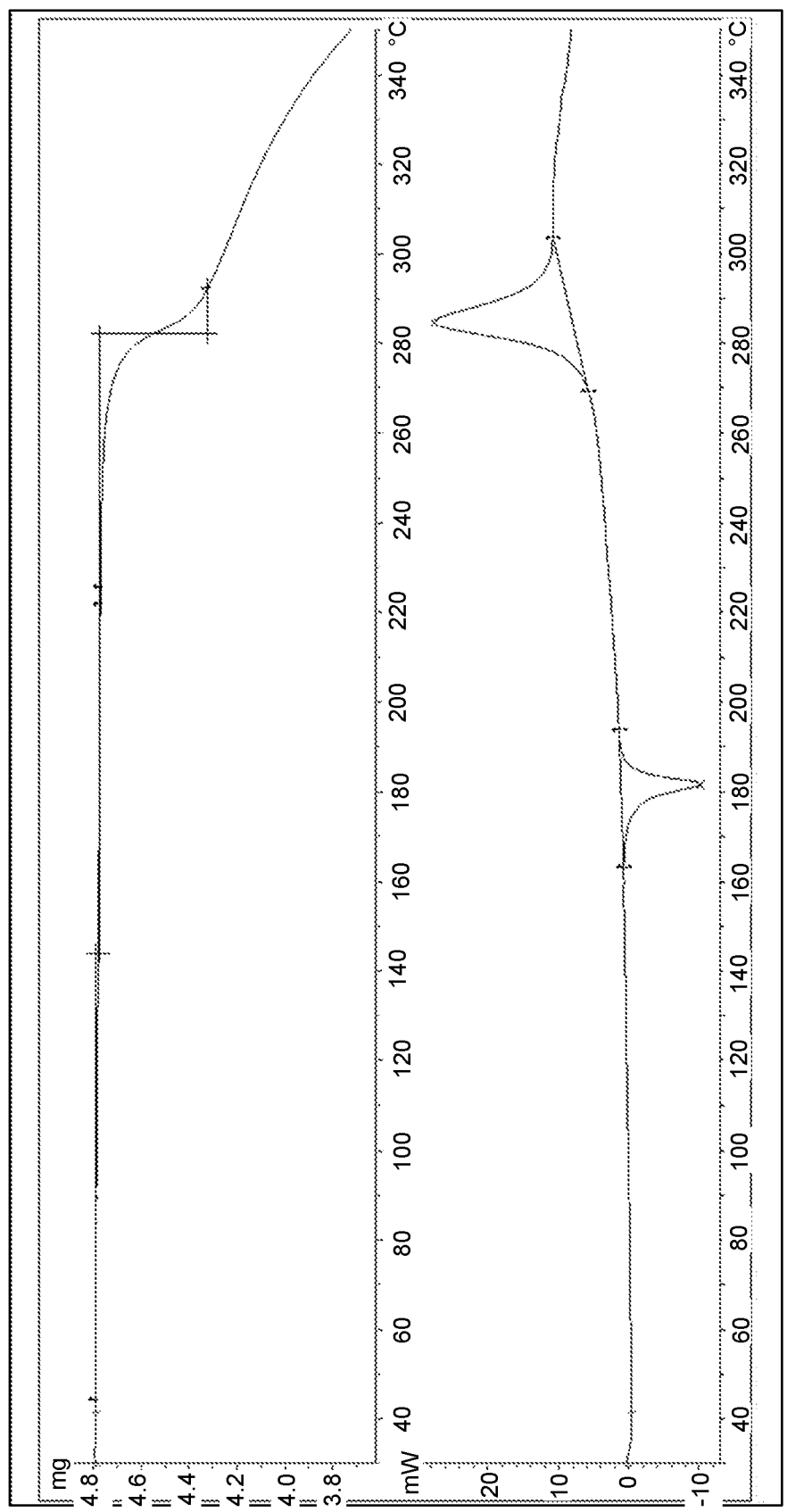
FIG. 6 depicts the TGA-DSC thermogram of the ITI-007 mono-tosylate salt crystal obtained from Example 2.

The DSC/TGA thermogram is shown in FIG. 6. DSC/TGA analysis shows one endothermic event at about 179° C., and one exothermic event at about 285° C. The first endothermic event occurs at about $T_{onset}=175°$ C., with a $T_{peak}=179°$ C. and a $\Delta E=-81$ J/g. The second exothermic event occurs at about $T_{onset}=278°$ C., with a $T_{peak}=285°$ C. and a $\Delta E=255$ J/g. The endothermic event is a melt, while the exothermic event is a recrystallization. The TGA profile shows a mass loss of 0.4% from 40° C. to 220° C., and a mass loss of 9.4% from 220° C. to 290° C.

LC-MS analysis shows a purity of 93 area % for the obtained solid.

Figure 7:
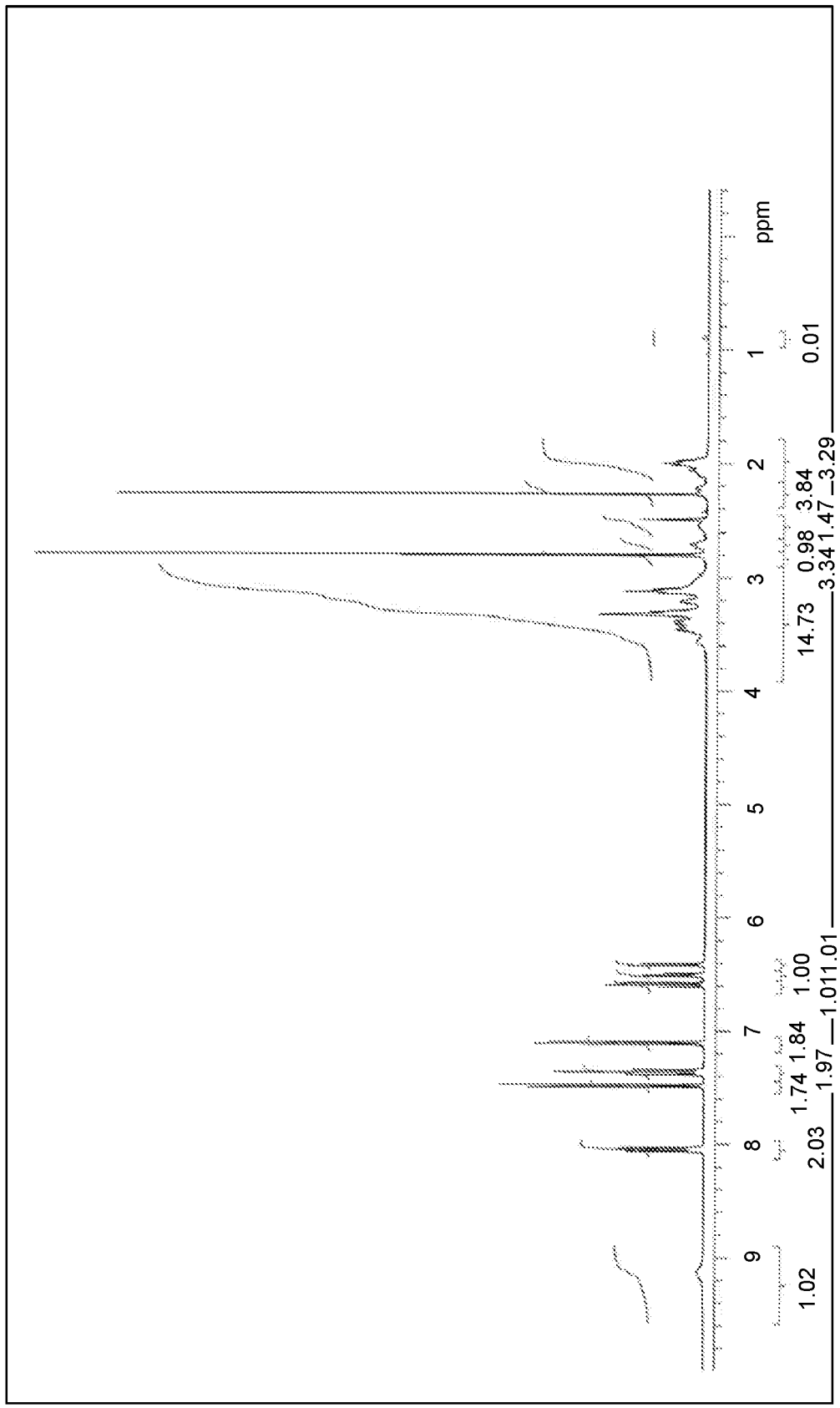
FIG. 7 depicts the 1H-NMR spectrum of the ITI-007 mono-tosylate salt crystal obtained from Example 2.

Proton NMR is shown in FIG. 7. Proton NMR analysis shows that the compound is the mono-tosylate salt of ITI-007. Specifically, the spectrum proton NMR spectrum shows the presence of one toluenesulfonic acid moiety per ITI-007 base moiety. This is demonstrated by the NMR protons at about 7.11 ppm, 7.36 ppm, 7.52 ppm and 8.05 ppm, which are present at an integral ratio of about 2:2:2:2. The 7.11 and 7.52 ppm peaks represent protons from the aromatic tosylate ring, while the 7.36 and 8.05 peaks represent protons from the aromatic 4-fluorophenyl ring of the ITI-007 free base. The remaining aromatic peaks between 6.4 and 7.0 ppm represent the aromatic protons of the quinoxaline core of ITI-007 and their integral is consistent with one molar unit of ITI-007 free base (integrals in a 1:1:1 ratio of clearly distinct peaks). The alkyl peak at about 2.3 ppm represents the methyl group of the tosylate ring and its integral is also consistent with one molar unit of toluenesulfonic acid.

Analytical results are summarized in Table 4 below.

TABLE 4

Analytical results for ITI-007 Mono-tosylate Salt of Example 2

| Solvent | Appearance | DSC ($T_{peak}$ ° C.) | DSC ($\Delta EJ/g$) | TGA: Mass loss (%) | HPLC purity (area %) |
|---|---|---|---|---|---|
| 2-Butanone | White solid | 179 | −81 | 0.4 | 93. |
| | | 285 | +255 | 9.4 | |

The invention claimed is:

1. A method of making a bis-tosylate salt of 1-(4-fluoro-phenyl)-4-((6bR,10aS)-3-methyl-2,3,6b,9,10,10a-hexa-hydro-1H,7H-pyrido[3',4': 4,5]pyrrolo[1,2,3-de]quinoxalin-8-yl)-butan-1-one, comprising the steps of:
   (a) reacting 1-(4-fluoro-phenyl)-4-((6bR,10aS)-3-methyl-2,3,6b,9,10,10a-hexahydro-1H,7H-pyrido[3',4': 4,5] pyrrolo[1,2,3-de]quinoxalin-8-yl)-butan-1-one (ITI-007) free base with toluenesulfonic acid at a molar ratio of about 1:1, in a solvent consisting of 2-butanone; and
   (b) recovering the salt thus formed as a crystalline solid by crystallization from the 2-butanone solvent, wherein the salt recovered contains less than 3 wt % of any other ITI-007 tosylate salt form, by weight of the salt.

2. The method according to claim 1, wherein in step (a) the salt is formed from a slurry of the ITI-007 free base and the toluenesulfonic acid in the 2-butanone solvent.

3. The method according to claim 1, wherein in step (b) the salt recovered contains less than 2 wt % of any other ITI-007 tosylate salt form, by weight of the salt.

4. The method according to claim 1, wherein the reaction of step (a) is carried out using the ITI-007 free base at a concentration of about 1 gram per 20 mL of the 2-butanone solvent.

5. The method according to claim 1, wherein in step (b) the salt recovered is isolated by filtration from the 2-butanone solvent to yield the crystalline solid.

6. The method according to claim 1, wherein the reaction of step (a) occurs at room temperature.

7. The method according to claim 1, wherein in step (b) the salt recovered contains less than 1 wt % of any other ITI-007 tosylate salt form, by weight of the salt.

8. The method according to claim 1, wherein in step (b) the salt recovered contains less than 5 wt % of ITI-007 free base form, by weight of the salt.

9. The method according to claim 1, wherein in step (b) the salt recovered contains less than 1 wt. % of any amorphous forms of ITI-007, by weight of the salt.

* * * * *